United States Patent [19]

Grollier et al.

[11] Patent Number: 4,673,568

[45] Date of Patent: Jun. 16, 1987

[54] HAIR-CARE COMPOSITION AND HAIR TREATMENT PROCESS

[75] Inventors: Jean F. Grollier, Paris; Claude Dubief, Le Chesnay; Daniele Cauwet, Paris, all of France

[73] Assignee: L'Oreal, Paris, France

[21] Appl. No.: 687,968

[22] Filed: Dec. 31, 1984

[30] Foreign Application Priority Data

Apr. 13, 1984 [LU] Luxembourg ............................ 85303

[51] Int. Cl.⁴ .......................... A61K 7/06; A61K 7/09; A61K 9/12
[52] U.S. Cl. ........................................ 424/47; 424/70; 424/71; 424/72
[58] Field of Search ....................... 424/70, 47, 71, 72; 514/880, 881

[56] References Cited

U.S. PATENT DOCUMENTS

| | | | |
|---|---|---|---|
| 4,115,548 | 9/1978 | Marsh et al. | 424/70 |
| 4,472,375 | 9/1984 | Bolich et al. | 424/70 |
| 4,477,375 | 10/1984 | Grollier | 424/70 |
| 4,490,356 | 12/1984 | Sebag et al. | 424/70 |
| 4,526,781 | 7/1985 | Goldberg et al. | 424/70 |
| 4,529,586 | 7/1985 | De Marco et al. | 424/70 |
| 4,540,507 | 9/1985 | Grollier | 424/70 |
| 4,559,227 | 12/1985 | Chandra et al. | 424/70 |
| 4,563,347 | 1/1986 | Starch | 424/70 |

FOREIGN PATENT DOCUMENTS

| | | | |
|---|---|---|---|
| 0057837 | 8/1982 | European Pat. Off. | 424/70 |
| 2463612 | 2/1981 | France | 424/70 |
| 0050909 | 3/1982 | Japan | 424/70 |
| 0056414 | 4/1982 | Japan | 424/70 |
| 0064606 | 4/1982 | Japan | 424/70 |
| 2522657 | 9/1983 | Japan | 424/70 |

*Primary Examiner*—Dale R. Ore
*Attorney, Agent, or Firm*—Fleit, Jacobson, Cohn & Price

[57] ABSTRACT

Cosmetic composition for hair treatment and care containing at least one water-dispersible cationic surfactant, at least one water-soluble quaternized protein and at least one cationic silicone polymer.

This composition is a shampoo, a rinsed or non-rinsed lotion, a restructuring composition or a composition for blow-drying, or a composition for permanent-waving, which are in the form of dispersion, gel, or foam.

This composition confers advantageous cosmetic characteristics to hair in respect of disentangling, softness, shape-retention, liveliness and the absence of static electricity; it makes hair ends smoother and promotes quicker hair drying.

20 Claims, No Drawings

HAIR-CARE COMPOSITION AND HAIR TREATMENT PROCESS

The present invention relates to new cosmetic compositions for the treatment and care of hair, containing at least one water-dispersible cationic surfactant, at least one water-soluble quaternised protein, and at least one cationic silicone polymer.

It is well known that hair is generally sensitised in various degrees by the action of atmospheric agents and by the action of treatments such as bleaching, permanent-waving and/or dyeing, with the result that hair is frequently difficult to disentangle and to style.

One of the means generally employed for improving the disentangling and the softness of sensitised hair consists in using surfactants of a cationic nature.

However, the use of surfactants of a cationic nature has the disadvantage of making hair heavier and giving it an oily appearance.

This disadvantage is accentuated in the case of fine hair which is lacking in shape-retention, liveliness and bulk.

It has already been proposed elsewhere to improve the disentangling and softness of hair by employing quaternised proteins which do not have the disadvantage of making hair heavier and imparting an oily appearance. However, the disentangling obtained is inferior to that conferred by a cationic surfactant.

Compositions combining a surfactant of a cationic nature with a quaternised protein have also been proposed.

These combinations do not make it possible, however, to obtain the maximum of the properties conferred by the cationic surfactant and the quaternised protein, because in the majority of cases the deposition of the cation retards that of the quaternised protein.

Furthermore, hair-care compositions combining cationic polymers of the type of MERQUAT 100 and 550, ONAMER or quaternised polyvinylpyridines, with cationic silicone polymers of the Amodimethicone type have been proposed in French Patent Application No. 2,463,612 to produce some retention of the cosmetic properties.

However, these compositions still have disadvantages; in particular, they are still do not result in the required disentangling, liveliness and shape-retention.

We have discovered that, by combining in a hair-care cosmetic composition a water-dispersible cationic surfactant with a water-soluble quaternised protein and a cationic silicone polymer, simultaneous deposition of these three components on hair was promoted, thereby providing a cosmetic composition markedly superior to those known hitherto in respect of the properties of disentangling, softness, shape-retention and liveliness. The hair was at the same time light, resilient, shiny and antistatic and its feel and its appearance was very silky.

Compared to the compositions of the prior art, the composition according to the invention permits better treatment of hair ends, that is to say the most sensitised parts; it makes them smoother and easier to gather together in the wet or dry state, contributing to the improvement of the finish of the hairstyle.

Furthermore, and in particular in the case where the hair-care composition according to the invention requires a rinse, it makes hair resilient at the root more quickly and hair dries more quickly.

The present invention provides a cosmetic composition suitable for hair-care which comprises at least one water-dispersible cationic surfactant, at least one water-soluble quaternised protein, and at least one cationic silicone polymer.

The present invention also provides a process of hair treatment comprising applying to hair a suitable quantity of the abovementioned composition.

The cationic surfactants according to the invention are water-dispersible compounds, preferably of the formula (I):

in which:

1.
$R_1$ is a product of general formula:

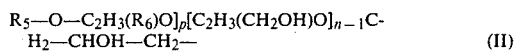

in which:

$R_5$ is a straight- or branched-chain saturated or unsaturated, aliphatic radical, and preferably an alkyl radical group of 4 to 20 carbon atoms;

$R_6$ is
(i) an alkyl, preferably straight-chain;
(ii) a straight- or branched-chain alkoxymethyl group;
(iii) a straight-chain alkenyloxy group, the alkyl or alkenyl parts of $R_6$ containing from 4 to 20 carbon atoms;

p is from 1 to 2.5 and is a mean statistical value;
n is from 2 to 20 and preferably from 2 to 15 and is a mean statistical value.

$R_2$ is an alkyl or hydroxyalkyl group of from 1 to 3 carbon atoms.

$R_3$ and $R_4$, which may be identical or different, are each an alkyl or hydroxyalkyl, group of from 1 to 3 carbon atoms and preferably methyl, ethyl, isopropyl or hydroxyethyl, or $R_3$ and $R_4$ form, with the nitrogen atom to which they are attached, a 5 or 6-membered heterocyclic ring and preferably a pyrrolidine, piperidine, morpholine or N-methylpiperazine heterocyclic ring.

$X^\ominus$ is an anion and preferably a methylsulphate, methanesulphonate, p-toluenesulphonate, bromide, chloride or iodide anion.

2.
$R_2$ and $R_3$ are each methyl; and,
$R_1$ and $R_4$ which may be identical or different are each a straight-chain saturated aliphatic group and preferably an alkyl group of from 12 to 22 carbon atoms or an aliphatic group derived from tallow fatty acids, containing from 14 to 22 carbon atoms; or
(ii) $R_1$ is a straight-chain saturated aliphatic group and preferably an alkyl group of from 14 to 22 carbon atoms and $R_4$ is methyl or benzyl; or,
(iii) $R_1$ denotes an alkylamidopropyl group ($C_{14}$–$C_{22}$ alkyl) and $R_4$ is an alkylacetate group ($C_{12}$–$C_{16}$ alkyl).

$X^\ominus$ is an anion such as a halide or $CH_3SO_4^\ominus$.

3.
$R_1$ is an alkylamidoethyl and/or an alkenylamidoethyl group where the alkyl and/or alkenyl group contains from 14 to 22 carbon atoms and is derived from tallow fatty acids and $R_2$ and $R_3$ form with the N to which they are attached a substituted heterocyclic ring of the 4,5-dihydroimidazole type, for example a 2-(tallow fatty acids derived)alkyl-4,5-dihydroimidazole heterocyclic ring:

$R_4$ is a $C_1$-$C_4$-alkyl, preferably methyl; and, $X^\ominus$ is $CH_3SO_4^\ominus$.

An example of such a cationic surfactant is the compound sold under the name "REWOQUAT W 7500".

Among the cationic surfactants of formula (I), the following are preferred:

(a)

$R_1$ is

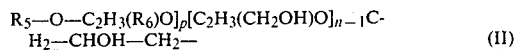

$$R_5-O-C_2H_3(R_6)O]_p[C_2H_3(CH_2OH)O]_{n-1}CH_2-CHOH-CH_2- \quad (II)$$

where $R_5$ is $C_8H_{17}$ or $C_{10}H_{21}$, $R_6$ is $C_{14}H_{29}$ or $C_{16}H_{33}$, p is 1, n is from 2 to 5, $R_2$ is methyl, $R_3$ and $R_4$ and the nitrogen atom to which they are attached form a morpholino ring; and, $X^\ominus$ is $CH_3SO_4^\ominus$ or $CH_3SO_3^\ominus$.

(b)

$R_1$ is $C_{10}H_{21}-O-C_2H_3(C_{14}H_{29})O][C_2H_3(CH_2OH)O]CH_2-CHOH-CH_2-$ (III)

$R_2$ is methyl, $R_3$ and $R_4$ and the nitrogen atom to which they are attached form a morpholino heterocyclic ring, and, $X^\ominus$ is $CH_3SO_3^\ominus$.

(c)

$R_1$ is $C_{10}H_{21}-O-C_2H_3(C_{14}H_{29})O][C_2H_3(CH_2OH)O]_4CH_2-CHOH-CH_2-$ (VI)

$R_2$ is methyl, $R_3$ and $R_4$ and the nitrogen atom to which they are attached form a morpholino heterocyclic ring; and $X^\ominus$ is $CH_3SO_3^\ominus$.

(d)

$R_1$ and $R_4$ are each a mixture of alkenyl and/or alkyl groups derived from tallow fatty acids and containing from 14 to 22 carbon atoms.

$R_2$ and $R_3$ are each methyl; and, $X^\ominus$ is $Cl^\ominus$.

(e)

$R_1$ is an alkylamidoethyl and/or alkenylamidoethyl group where the alkyl and/or alkenyl group contains from 14 to 22 carbon atoms and is derived from tallow fatty acids; $R_2$ and $R_3$ form with the N atom a 2-(tallow fatty acids derived)alkyl-4,5-dihydroimidazole heterocyclic ring;

$R_4$ is a $C_1$-$C_4$ alkyl; and, $X^\ominus$ is $CH_3SO_4^\ominus$ (f) $R_1$ is a straight-chain saturated aliphatic group of 22 carbon atoms and preferably a $C_{22}$ alkyl group;

$R_2$, $R_3$ and $R_4$ are each methyl;

$X^\ominus$ is $Cl^\ominus$.

The quaternary proteins used in the invention generally already known and have already been recommended for use in cosmetics.

They are usually chemically modified polypeptides carrying quaternary ammonium groups at the end of the chain or grafted on the chain.

Among these quaternised proteins mention may be made of:

collagen hydrolysates carrying triethylammonium groups, sold under the name of QUAT PRO E by the company MAYBROOK and called "Triethonium Hydrolyzed Collagen Ethosulfate" in the CTFA dictionary.

The "CTFA dictionary" is the "CTFA Cosmetic Dictionary", 3rd edition, 1982, published by The Cosmetic, Toiletry and Fragrance Association, Inc., 1133 Fifteenth Street NW Washington D.C. (USA).

collagen hydrolysates carrying trimethylammonium chloride and trimethylstearylammonium chloride groups, sold under the name of QUAT-PRO S by the company MAYBROOK and called "Stear-trimonium Hydrolyzed Collagen" in the CTFA dictionary;

animal protein hydrolysates carrying trimethylbenzylammonium groups, sold under the name "CROTEIN BTA" by the company CRODA and called "Benzyltrimonium hydrolyzed animal protein" in the CTFA dictionary;

protein hydrolysates carrying on the polypeptide chain quaternary ammonium groups containing at least one alkyl radical containing from 1 to 18 carbon atoms.

The most preferred of these protein hydrolysates are:

CROQUAT L, the peptide chain of which has an average molecular weight (M.W.) of approximately 2,500 and the ammonium group of which contains a $C_{12}$ alkyl.

CROQUAT M, the peptide chain of which has an average M.W. of approximately 2,500 and the ammonium group of which contains a $C_{10-18}$ alkyl.

CROQUAT S, the polypeptide chain of which has an average M.W. of approximately 2,700 and the ammonium group of which contains a $C_{18}$ alkyl.

CROTEIN Q, the polypeptide chain of which has an average M.W. of the order of 12,000 and the ammonium group of which contains at least one alkyl group containing from 1 to 18 carbon atoms.

The products CROQUAT L, CROQUAT M, CROQUAT S and CROTEIN Q are sold by the company CRODA.

The preferred quaternised proteins include those having the formula:

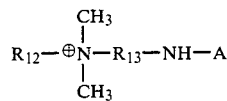

in which A denotes a protein residue derived from collagen protein hydrolysates, $R_{12}$ denotes a lipophilic group containing up to 30 carbon atoms, $R_{13}$ denotes an alkylene group containing 1 to 6 carbon atoms; of a molecular weight of from 1,500 to 10,000 and preferably from 2,000 5,000 such as the product sold under the name LEXEIN QX 3000 called "Cocotrimonium Collagen Hydrolysate" in the CTFA dictionary, and marketed by the company INOLEX.

Cationic silicone polymers which may be used in the composition according to the invention are eg. those mentioned in the CTFA dictionary under the name of Amodimethicone, of formula:

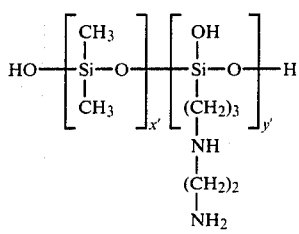

x' and y' are integers depending on the molecular weight, the average molecular weight being from 5,000 to 10,000.

A polymer which is especially preferred is that sold under the trade name of "Cationic Emulsion DC 929 or (DC 929)" by the company DOW CORNING and which is a combination of "Amodimethicone", of "tallowtrimonium chloride" of formula:

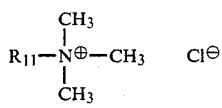

where $R_{11}$ denotes a mixture of alkenyl and/or alkyl radicals containing from 14 to 22 carbon atoms, derived from tallow fatty acids, and of "Nonoxynol 10" of formula:

$$C_9H_{19}-C_6H_4-(OC_2H_4)_{10}-OH$$

Cationic silicone polymers possible in the composition according to the invention also include those corresponding to the general formula:

$$R'_aG_{3-a}Si(OSiG_2)_n(OSi\ G_bR'_{2-b})_mO-Si\ G_{3-a}R'_a$$

in which:
G is chosen from the group consisting of H, OH, $C_{1-8}$ alkyl and phenyl, and preferably denotes methyl,
a denotes 0 or an integer from 1 to 3 and is preferably equal to 0,
b denotes 0 or 1 and is preferably equal to 1,
the sum (n+m) denotes a number from 1 to 2,000 and preferably from 50 to 150, n being capable of denoting a number from 0 to 1,999 and preferably from 49 to 149 and m being capable of denoting a number from 1 to 2,000 and preferably from 1 to 10.
R' is a monovalent radical of formula $C_qH_{2q}L$ in which q=2 to 8,
L being chosen from the groups:
N R''—CH$_2$—CH$_2$—N(R'')$_2$
N (R'')$_2$
N$^\oplus$(R'')$_3$ A$^\ominus$
N$^\oplus$(R'')H$_2$ A$^\ominus$
NR''CH$_2$—CH$_2$—N$^\ominus$R''H$_2$ A$^\ominus$
in which R'' is chosen from the group consisting of H, phenyl, benzyl, and a saturated monovalent hydrocarbon radical, preferably an alkyl radical containing from 1 to 20 carbon atoms,
A$^\ominus$ denotes a halide ion (Cl$^\ominus$, Br$^\ominus$, I$^\ominus$ or F$^\ominus$).

These compounds are described in greater detail in European Patent Application EP No. 95,238. A polymer which is especially preferred is that sold by the company DOW CORNING under the name "DOW CORNING Q2 7224" which is a combination of:
(a) trimethylsilylamodimethicone of formula:

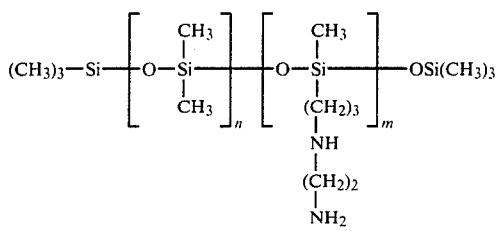

n and m having the abovementioned meanings.
(b) octoxynol-40 of formula:

$$C_{18}H_{17}-C_6H_4-(OCH_2CH_2)_nOH$$

where n=40
(c) isolaureth-6 of formula:

$$C_{12}H_{25}-(OCH_2-CH_2)_nOH$$

where n=6
(d) and glycol.

Other cationic silicone polymers which may be used in the composition according to the invention are those corresponding to the general formula:

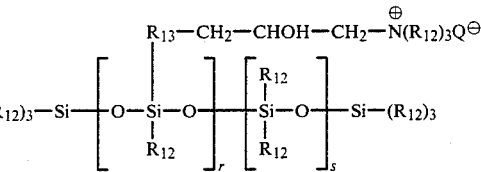

in which:
$R_{12}$ denotes a monovalent hydrocarbon radical containing from 1 to 18 carbon atoms, in particular an alkyl or alkenyl radical, and preferably methyl,
$R_{13}$ denotes a divalent hydrocarbon radical, preferably a $C_1$-$C_{18}$ alkylene radical or a divalent $C_1$-$C_{18}$, and preferably $C_1$-$C_8$, alkylenoxy radical,
$Q^\ominus$ is a halide ion (preferably chloride),
r denotes a mean statistical value from 2 to 20 and preferably from 2 to 8,
s denotes a mean statistical value from 20 to 200 and preferably from 20 to 50.

These compounds are described in greater detail in U.S. Pat. No. 4,185,087.

A cationic silicone polymer which is especially preferred is that sold by the company UNION CARBIDE under the name "UCAR SILICONE ALE 56" which is characterised by a flashpoint, according to the ASTM Standard D-93, of 60° C., by a viscosity of 11 centipoises at a concentration of 35% of active material and at 25° C., and a total basicity value of 0.24 milliequivalent/gramme (meq/g).

A cosmetic hair-care composition which is especially preferred according to the invention contains: at least one cationic surfactant of formula (I):

in proportions of from 0.5 to 1.5% by weight of the total weight of the composition, at least one quaternised protein, in proportions of from 0.1 to 0.6% by weight of the total weight of the composition, and at least one silicone polymer such as DOW's DC 929 in proportions of from 0.5 to 1.5% by weight of the total weight of the composition.

The cationic surfactants are preferably present in the hair-care composition according to the invention in proportions of from 0.05 to 7%, and more preferably from 0.1 to 3%, by weight of the total weight of the composition.

The water-soluble quaternised proteins are preferably present in the cosmetic hair-care composition according to the invention in proportions of from 0.05 to 7%, and more preferably from 0.1 to 3%, by weight, of the total weight of the composition.

The cationic silicone polymers are preferably present in the cosmetic hair-care composition according to the invention in proportions of from 0.05 to 7%, and more preferably from 0.1 to 3%, by weight of the total weight of the composition.

The cosmetic hair-care compositions according to the invention may be in the form of aqueous or aqueous-alcoholic dispersions, thickened or unthickened, cream, gel, aerosol foam or spray.

They may contain, in addition to one or more water-dispersible cationic surfactants, one or more water-soluble quaternised proteins and one or more silicone polymers, adjuvants usually employed in cosmetics, such as perfumes, colorants, preserving agents, sequestering agents, thickeners, emulsifiers, softeners, foam stabilisers, and other adjuvants usually employed in hair-care compositions, depending on the intended application.

The cosmetic hair-care compositions according to the invention may be applied in the form of shampoo, after-shampoo composition, rinse products to be applied before or after a shampoo, before or after colouring or bleaching, before or after a permanent-wave or hair straightening, lotions for hairsetting or for blow-drying, lotions which are not rinsed, restructuring compositions, or products for permanent waves.

When the composition forms a shampoo, generally it also contains one or more anionic, nonionic, amphoteric and/or zwitterionic surfactants, the total surfactant concentration being generally from 3 to 50% and preferably from 3 to 20% by weight of the total weight of the composition.

The pH is generally from 3 to 10.

The compositions according to the invention can also be rinsing products. These products may be aqueous or aqueous-alcoholic dispersions, emulsions, thickened compositions or gels.

When the compositions are in the form of emulsions, they may be nonionic or anionic.

When the compositions are in thickened form or are gels, usually they contain thickeners in the presence or absence of solvents.

The thickeners which can be employed may be sodium alginate or gum arabic, cellulose derivatives such as methyl cellulose, hydroxymethyl cellulose, hydroxyethyl cellulose, hydroxypropyl cellulose, hydroxypropylmethyl cellulose, carboxymethyl cellulose, guar gum or its derivatives. Thickening of the compositions may also be obtained with a mixture of polyethylene glycol and polyethylene glycol stearate or distearate or with a mixture of phosphoric ester and amide.

The concentration of thickener may vary from 0.1 to 30% by weight and preferably from 0.2 to 15% by weight.

The pH of the rinsing products varies mainly from 3 to 9%.

When the compositions according to the invention are in the form of products for hairstyling or shaping or setting, they generally contain the components of the abovementioned combination and, if appropriate, antifoaming agents and nonionic polymers, in aqueous, alcoholic, or aqueous-alcoholic dispersion.

The composition according to the invention may also be employed in compositions intended for curling hair (permanent waving). The conventional technique of this permanent-waving consists in first applying a composition containing a reducing agent and then, after the hair has, if appropriate, been rinsed, applying a composition containing an oxidising agent. According to the invention, at least one of the two compositions contains the composition as described earlier.

The various hair-care compositions according to the invention are advantageously offered under pressure, in the form of an aerosol can, and are employed in the form of aerosol foam. In this case, they contain one or more gaseous propellants.

The gaseous propellants employed for pressurising the cosmetic formulations are present in proportions which do not exceed 25% and preferably 15% relative to the total weight of the composition. Carbon dioxide, nitrogen, nitrous oxide, volatile hydrocarbons such as butane, isobutane, propane and their mixtures, non-hydrolysable chlorinated and/or fluorinated hydrocarbons such as, for example, those sold under the name FREON by the company DuPont de Nemours, and belonging, in particular, to the groups of fluorochlorohydrocarbons such as dichlorodifluoromethane or Freon 12, dichlorotetrafluoroethane or Freon 114, may be used as gaseous propellant. These propellants may be employed alone or in combination; in particular mention may be made of the Freon mixture 114-12 in proportions ranging from 40:60 to 80:20.

The pH of these compositions may be adjusted with an alkalising or acidifying agent usually employed in the field of cosmetics. The pH is generally from 3 to 10, depending on the intended application. It is adjusted with the aid of alkalising or acidifying agents which are well known in the state of the art.

The invention is best illustrated with the aid of the following non-restrictive examples.

EXAMPLE 1

An after-shampoo in aerosol form is prepared, with the following composition:

| | |
|---|---|
| Distearyldimethylammonium chloride | 2 g AS (active substance) |
| Hydrolysate of a protein containing a polypeptide chain with a M.W. of about 2,500 and quaternary ammonium groups with $C_{12}$ alkyl groups, sold under the name CROQUAT L by the company CRODA at a concentration of 40% AS | 0.3 g AS |
| Cationic emulsion which is a combination: | |
| of Amodimethicone, of tallowtrimonium, and of Nonoxinol 10, sold by the company DOW CORNING under the name "Cationic Emulsion DC 929" at the concentration of 35% AS | 0.3 g AS |

-continued

| | |
|---|---|
| Perfume, preserving agent, colorant q.s. | |
| NaOH q.s. pH 6.4 | |
| Water q.s. | 100 g |

This composition is packaged as aerosol:

| | |
|---|---|
| Above composition | 90 g |
| Propellant: Freons 12/114 (50/50 by weight) | 10 g |
| Total: | 100 g |

The foam is applied to clean hair and left in contact for a few minutes.

After rinsing, the wet hair is supple, soft and lively (good restoration of curliness).

When dry, the hair is soft, shiny, and disentangles easily.

EXAMPLE 2

A rinsing lotion is prepared, with the following composition:

| | |
|---|---|
| Cationic surfactant of formula: | 1 g AS |

$$C_{10}H_{21}O\!\!-\!\!\!\left[C_2H_3(C_{14}H_{29})O\right]\!\!-\!\!\left[C_2H_3(CH_2OH)O\right]\!\!-\!\!CH_2\!\!-\!\!CHOH\!\!-\!\!CH_2\!\!-\!\!\overset{\oplus}{N}\!\!\!\underset{CH_3}{\diagdown}\!\!\!\diagup\!\!O$$

$$CH_3SO_4^{\ominus}$$

| | |
|---|---|
| Hydrolysate of a protein containing a polypeptide chain with a M.W. of about 12,000 and quaternary ammonium groups containing at least one C₁–18 alkyl group, sold under the name CROTEIN Q by the company CRODA | 0.5 g AS |
| Cationic emulsion which is a combination: of Amodimethicone, of tallowtrimonium, and of Nonoxinol 10, sold by the company DOW CORNING under the name "Cationic Emulsion DC 929" at the concentration of 35% AS | 2 g AS |
| Perfume, preserving agent, colorant q.s. | |
| HCl q.s. pH 5 | |
| Water q.s. | 100 g |

This rinsing lotion produces disentanglement, softness, suppleness and lightness in wet hair, it facilitates the disentangling of dried hair, endowing it with softness and sheen, and, on highly sensitised hair, a slight improvement in the holding of the style is noticed.

EXAMPLE 3

An after-shampoo composition is prepared with the following composition:

| | |
|---|---|
| Stearyldimethylbenzylammonium chloride | 1.5 g AS |
| Quaternised protein, called "Cocotrimonium Collagen Hydrolysate" in the CTFA dictionary, sold under the name LEXEIN QX 3000 by the company INOLEX at a concentration of 30% AS | 2 g AS |
| Cationic emulsion which is a combination: | |
| of Amodimethicone, of Tallowtrimonium, and of Nonoxinol 10, sold by the company DOW CORNING under the name "Cationic Emulsion DC 929" at a concentration of 35% AS | 1.5 g AS |
| Hydroxyethyl cellulose sold under the name of NATROSOL 250 HHR by the HERCULES company | 1.2 g AS |
| Coconut oil cycloimidazoline derivative sold under the name MIRANOL C 2 M | 0.5 g AS |

-continued

| | |
|---|---|
| by the company MIRANOL at a concentration of 38% AS | |
| Perfume, preserving agent, colorant q.s. | |
| pH = 7.4 adjusted with triethanolamine | |
| Water q.s. | 100 g |

This composition is applied to clean hair and left in contact for a few minutes.

After rinsing, the wet hair is supple.

When dry, the hair disentangles very easily. It is soft and lively.

EXAMPLE 4

An after-shampoo composition is prepared with the following composition:

| | |
|---|---|
| Behenyltrimethylammonium chloride | 0.2 g AS |
| Collagen hydrolysate containing triethylammonium groups and called "Triethonium Hydrolyzed Collagen Ethosulfate" in the CTFA dictionary, sold under the name QUAT PRO S by the company CRODA | 0.5 g AS |
| Cationic emulsion which is a combination: | |
| of Amodimethidone, of Tallowtrimonium, and of Nonoxinol 10, sold by the company DOW CORNING under the name "Cationic Emulsion DC 929" at a concentration of 35% AS | 1 g AS |
| Carboxymethyl cellulose sold by the HERCULES company | 1.5 g AS |
| Perfume, preserving agent, colorant q.s. | |
| NaOH q.s. pH 7.5 | |
| Water q.s. | 100 g |

This composition, applied to clean wet hair, makes it soft, light and supple, and facilitates disentangling.

After being dried, the hair is readily disentangled, is soft and shiny, resilient lively and well-behaved. A slight improvement in the holding of the style and a marked improvement in the condition of the ends is observed in sensitised hair.

EXAMPLE 5

A rinsed lotion is prepared, with the following composition:

Stearamidopropyldimethyl(myristyl acetate)ammonium chloride, of formula:

| | |
|---|---|
| $R-CONH(CH_2)_3-\overset{\oplus}{\underset{CH_3}{\overset{CH_3}{N}}}-CH_2-COOC_{14}H_{29} \quad Cl^{\ominus}$ | where R = stearyl |
| sold by the company VAN DYK under the name CERAPHYL 70 at a concentration of 70% AS | 1.5 g AS |
| Animal protein hydrolysate containing trimethylbenzylammonium groups and called "Benzyltrimonium hydrolyzed animal protein" in the CTFA dictionary, sold by the company CRODA under the name CROTEIN BTA, at a concentration of 33.3% AS | 0.3 g AS |
| Cationic silicone polymer with a flashpoint of 60° C., according to ASTM D-93, a viscosity of 11 centipoises at a concentration of 35% AS and at 25° C., and a total basicity value of 0.24 meq/g, sold by the company UNION CARBIDE under the name UCAR SILICONE ALE 56 at a concentration of 35% AS | 0.2 g AS |
| Perfume, preserving agent, colorant q.s. NaOH q.s. pH 6 | |
| Water q.s. | 100 g |

The composition is applied to clean, wet hair after a shampoo. A contact time of a few minutes is used; after rinsing, the wet hair disentangles readily and is supple and soft. Dried sensitised hair is soft, lively, very shiny and silky down to the ends and disentangles readily.

EXAMPLE 6

A rinsed lotion with the following composition is prepared:
Stearamidopropyldimethyl(myristyl acetate)ammonium chloride, of formula:

| | |
|---|---|
| $R-CONH(CH_2)_3-\overset{\oplus}{\underset{CH_3}{\overset{CH_3}{N}}}-CH_2-COOC_{14}H_{29}$ | where R = stearyl |
| sold by the company VAN DYK under the name of CERAPHYL 70 at a concentration of 70% AS | 0.4 g AS |
| Collagen hydrolysate containing triethylammonium groups called "Triethonium Hydrolyzed Collagen Ethosulfate" in the CTFA dictionary, sold under the name QUAT PRO E by the company MAYBROOK | 0.9 g AS |
| Cationic emulsion which is a combination: of Amodimethicone, of Tallowtrimonium, and of Nonoxinol 10, sold by the company DOW CORNING under the name CATIONIC EMULSION DC 929 at a concentration of 35% AS | 1.2 g AS |
| Mixture of cetylstearyl alcohol and cetylstearyl alcohol oxyethylenated with 15 moles of ethylene oxide, sold under the name SINNOWAX A0 by the company HENKEL | 3.5 g AS |
| Mixture of fatty alcohol and of oxyethylenated products, sold by the company CRODA under the name POLAWAX GP 200 | 1.5 g AS |
| Hydroxyethyl cellulose with a viscosity of 4,400 cP (at 2% concentration in aqueous solution at 25° C. using Brookfield unit 4), sold by the company UNION CARBIDE under the name CELLOSIZE QP 4400 H | 0.2 g AS |
| Perfume, preserving agent, colorant q.s. NaOH q.s. pH 5 | |
| Water q.s. | 100 g |

The composition is applied to clean, wet hair after a shampoo. A contact time of a few minutes is used. After rinsing, the wet hair disentangles very readily, and is supple and soft.

Dried and sensitised hair is soft, lively, very shiny and silky down to the ends and disentangles readily.

EXAMPLE 7

A blow-drying lotion is prepared, with the following composition:
Stearamidopropyldimethyl(myristyl acetate)ammonium chloride, of formula:

| | |
|---|---|
| $R-CONH-(CH_2)_3-\overset{\oplus}{\underset{CH_3}{\overset{CH_3}{N}}}-CH_2-COOC_{14}H_{29}$ | where R = stearyl |
| sold by the company VAN DYK under the name CERAPHYL 70 at a concentration of 70% AS | 1.0 g AS |
| Collagen hydrolysate containing triethylammonium groups called "Triethonium Hydrolyzed Collagen Ethosulfate" in the CTFA dictionary, sold under the name QUAT PRO E by the company MAYBROOK | 0.2 g AS |
| Cationic emulsion which is a combination: (a) of trimethylsilylamodimethicone, (b) of octoxynol-40, (c) of isolaureth-6, and (d) of glycol, sold by the company DOW CORNING under the name DOW CORNING Q2 7224 at a concentration of 35% AS | 0.5 g AS |
| Polyvinylpyrrolidone/vinyl acetate copolymer [PVP/VA - 60%/40%] | 1.0 g AS |
| Ethyl alcohol | 20.0 g AS |
| Lactic acid q.s. pH 5 | |
| Perfume, colorant, preserving agent q.s. | |
| Water q.s. | 100 g |

This lotion is applied to dry hair before it is set.

After drying, the sensitised hair disentangles readily. The hair is lively, soft and shiny down to the ends and the styling is resilient and has good shape-retention.

EXAMPLE 8

A shampoo is prepared, with the following composition:
Stearamidopropyldimethyl(myristyl acetate)ammonium chloride, of formula:

| | |
|---|---|
| $R-CONH-(CH_2)_3-\overset{\oplus}{\underset{CH_3}{\overset{CH_3}{N}}}-CH_2-COOC_{14}H_{29}$ | where R = stearyl |
| sold by the company VAN DYK under the name CERAPHYL 70 at a concentration of 70% AS | 1 g AS |
| Protein hydrolysate containing a polypeptide chain with a M.W. of approximately 2,500 and quaternary ammonium groups containing $C_{10-18}$ alkyl groups, | 0.7 g AS |

| | |
|---|---|
| sold under the name CROQUAT M by the company CRODA at a concentration of 44.4% AS | |
| Cationic emulsion which is a combination: of Amodimethicone, of Tallowtrimonium, and of Nonoxinol 10, sold by the company DOW CORNING under the name "Cationic Emulsion DC 929" at a concentration of 35% AS | 2 g AS |
| Sodium alkyl($C_{12-14}$) ether sulphate oxyethylenated with 2.2 moles of ethylene oxide, at a concentration of 25% AS | 8 g AS |
| Perfume, preserving agent, colorant q.s. HCl q.s. pH 7.1 | |
| Water q.s. | 100 g |

EXAMPLE 9

A shampoo is prepared, with the following composition:
Quaternary ammonium salt of formula:

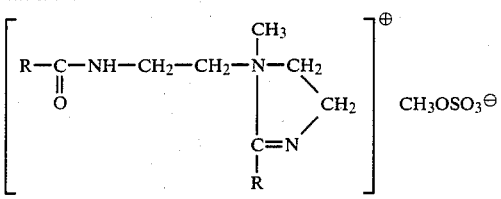

| | |
|---|---|
| R denoting a "mixture of alkenyl and/or alkyl radicals containing from 14 to 22 carbon atoms derived from tallow fatty acids", sold by the company REWO under the name REWOQUAT W7500 at a concentration of 78% AS | 2 g AS |
| Animal protein hydrolysate containing trimethylbenzylammonium groups and called "Benzyltrimonium hydrolyzed animal protein" in the CTFA dictionary, sold by the company CRODA under the name CROTEIN BTA, at a concentration of 33.3% AS | 0.3 g AS |
| Cationic emulsion which is a combination: of Amodimethicone, of Tallowtrimonium, and of Nonoxinol 10, sold by the company DOW CORNING under the name "Cationic Emulsion DC 929" at a concentration of 35% AS | 0.7 g AS |
| Coconut oil cycloimidazoline derivative sold by the company MIRANOL under the name MIRANOL 0.2 M at a concentration of 38% AS | 5 g AS |
| $C_{12}$–$C_{18}$-alkyldimethylcarboxymethyl-ammonium hydroxide, sold under the name DEHYTON AB 30 by the company HENKEL | 3 g AS |
| Perfume, preserving agent, colorant q.s. HCl q.s. pH 7.2 | |
| Water q.s. | 100 g |

EXAMPLE 10

A shampoo is prepared, with the following composition:

| | |
|---|---|
| Stearamidopropyldimethyl (myristyl acetate) ammonium chloride, sold by the company VAN DYK under the name CERAPHYL 70 at a concentration of 70% AS | 1.2 g AS |
| Protein hydrolysate containing a poly-peptide chain with a M.W. of approximately 2,500 and quaternary ammonium groups containing $C_{18}$ alkyl groups, sold by the company CRODA under the name CROQUAT S at a concentration of 43.7% AS | 0.5 g AS |
| Cationic silicone polymer with a flashpoint of 60° C. according to ASTM D-93 a viscosity of 11 centipoises at a concentration of 35% AS and at 25° C., and a total basicity value of 0.24 meq/g, sold by the company UNION CARBIDE under the name "UCAR SILICONE ALE 56" at a concentration of 35% AS | 0.8 g AS |
| Sodium salt of tridecetyl-7 carboxylic acid of formula: $CH_3$—$(CH_2)_{11}$—$CH_2$—$(OCH_2$—$CH_2)_6OCH_2$—COONa sold by the company SANDOZ under the name SANDOPAN DTC, at a concentration of 90% AS | 5 g AS |
| Sodium and magnesium lauryl ether sulphate, sold by the company HENKEL under the name TEXAPON ASV at the concentration of 30% AS | 3 g AS |
| Perfume, preserving agent, colorant q.s. NaOH q.s. pH 6.5 | |
| Water q.s. | 100 g |

Hair washed by means of the shampoos in Examples 8, 9 or 10 is soft and can be easily disentangled when wet. Dry sensitised hair is resilient, lively, light, silky, soft, shiny and smooth down to the ends.

EXAMPLE 11

A rinsed lotion is prepared, with the following composition:

| | |
|---|---|
| Distearyldimethylammonium chloride | 0.8 g AS |
| Quaternised protein called "Cocotrimonium Collagen Hydrolysate" in the CTFA dictionary, sold under the name LEXEIN QX 3000 by the company INOLEX at a concentration of 30% AS | 0.9 g AS |
| Cationic emulsion which is a combination: (a) of trimethylsilylamodimethicone, (b) of octoxynol-40, (c) of isolaureth-6, and (d) of glycol, sold by the company DOW CORNING under the name DOW CORNING Q2 7224 at a concentration of 35% of active substance | 0.3 g AS |
| Perfume, preserving agent, colorant q.s NaOH q.s. pH 7 | |
| Water q.s. | 100 g |

EXAMPLE 12

Permanent deformation of hair is carried out by applying the following reducing composition to all of the hair:

| | |
|---|---|
| Thioglycolic acid | 8.0 g |
| Ammonia solution q.s. pH 7 | |
| Ammonium bicarbonate | 6.4 g |
| Oleyl alcohol oxyethylenated with 20 moles of ethylene oxide | 1.0 g |
| Perfume q.s. | |
| Water q.s. | 100 g |

The hair is then wound on rollers and the treatment to act for 5 to 15 minutes. After careful rinsing, the following oxidising composition is applied:

| | |
|---|---|
| Phenacetin | 0.1 g |
| Citric acid | 0.3 g |
| Distearyldimethylammonium chloride | 0.5 g AS |
| Cationic emulsion which is a | |

-continued

| | |
|---|---|
| combination: | |
| of Amodimethicone, | 0.5 g AS |
| of Tallowtrimonium, and | |
| of Nonoxinol 10, sold by the company DOW CORNING under the name "Cationic Emulsion DC 929" at a concentration of 35% AS | |
| Quaternised protein called "Cocotrimonium Collagen Hydrolysate" in the CTFA dictionary, sold under the name LEXEIN QX 3000 by the company INOLEX at a concentration of 30% AS | 0.25 g AS |
| Nonylphenol oxyethylenated with 9 moles of ethylene oxide | 1 g |
| Hydrogen peroxide q.s. | 8 volumes |
| Colorant q.s. | |
| Water q.s. | 100 g |

The oxidising composition is left to act for 10 minutes. The hair is rinsed and dried.

Wet hair is easily disentangled and feels soft. After being dried, the hair is shiny and is readily disentangled; it feels very silky and the ends are smooth.

EXAMPLE 13

A non-rinsed lotion is prepared, with the following composition:

| | |
|---|---|
| Collagen hydrolysate containing trimethylammonium chloride and trimethyl- stearylammonium chloride groups, called "Steartrimonium Hydrolyzed Collagen" in the CTFA dictionary, sold under the name QUAT PRO S by the the company CRODA | 0.2 g AS |
| Quaternary ammonium salt of formula: | 1 g AS |

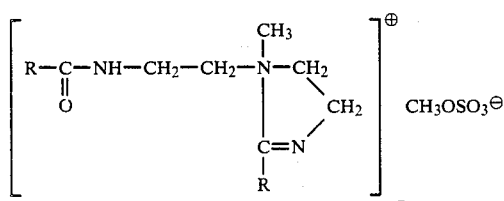

R denoting a "mixture of alkenyl and/or alkyl radicals containing from 14 to 22 carbon atoms derived from tallow fatty acids", sold by the company REWO under the name REWOQUAT W7500 at a concentration -continued

| | |
|---|---|
| of 78% AS | |
| Cationic emulsion which is a combination: of Amodimethicone, and of Tallowtrimonium, and of Nonoxinol 10, sold by the company DOW CORNING under the name "Cationic Emulsion DC 929" at a concentration of 35% AS | 1 g AS |
| Ethyl alcohol q.s. | 20 g |
| Lactic acid q.s. pH 5 | |
| Perfume, colorant, preserving agent, q.s. | |
| Water q.s. | 100 g |

This composition is packaged as an aerosol:

| | |
|---|---|
| Above composition | 90 g |
| Propellant: Freons 12/114 (50/50 by weight) | 10 g |
| Total: | 100 g |

The foam is applied to clean hair before setting or blow-drying.

After drying, the sensitised hair is soft and silky, shiny and disentangles readily; the ends are smooth and the styling is resilient and has good shape-retention.

EXAMPLE 14

A non-rinsed lotion is prepared, with the following composition:

| A non-rinsed lotion is prepared, with the following composition: | |
|---|---|
| Protein hydrolysate containing quaternary ammonium groups carrying at least one $C_{1-18}$ alkyl group, sold under the name CROTEIN Q by the company CRODA | 0.25 g AS |
| Cationic silicone polymer with a flashpoint of 60° C., according to ASTM D-93 a viscosity of 11 centipoises at a concentration of 35% AS and at 25° C., and a total basicity value of 0.24 meq/g, sold by the company UNION CARBIDE under the name UCAR SILICONE ALE 56 at a concentration of 35% AS | 0.35 g AS |
| Cationic surfactant of formula: | 0.4 g AS |

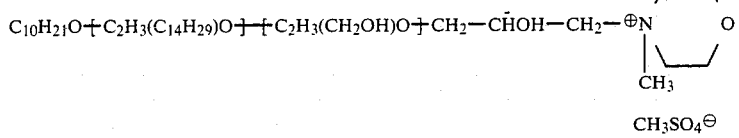

| | |
|---|---|
| Ethyl alcohol q.s. | 20 g |
| 2-Amino-2-methyl-1-propanol q.s. pH 7 | |
| Perfume, colorant, preserving agent q.s. | |
| Water q.s. | 100 g |

This composition is packaged as an aerosol.

| | |
|---|---|
| Above composition | 90 g |
| Propellant: Freons 12/114 (50/50 by weight) | 10 g |
| Total: | 100 g |

The foam is applied to clean hair before setting or blow-drying.

After drying, the sensitised hair is soft and silky, shiny, and disentangles readily; the ends are smooth and the styling is resilient and has good shape-retention.

EXAMPLE 15

An after-shampoo is prepared in the form of an aerosol, with the following composition:

| | |
|---|---|
| Quaternised protein called "Cocotrimonium Collagen Hydrolysate" in the CTFA dictionary, sold under the name LEXEIN QX 3000 by the company INOLEX at a concentration of 30% AS | 1.5 g AS |
| Cationic emulsion which is a combination: | |
| (a) of trimethylsilylamodimethicone, (b) of octoxynol-40, (c) of isolaureth-6, and (d) of glycol, sold by the company DOW CORNING under the name DOW CORNING Q2 7224 at a concentration of 35% AS | 0.5 g AS |
| Behenyltrimethylammonium chloride | 1 g AS |
| HCl q.s. pH 5 | |
| Perfume, preserving agent, colorant q.s. | |
| Water q.s. | 100 g |

This composition is packaged as an aerosol:

| | |
|---|---|
| Above composition | 90 g |
| Propellant: Freons 12/114 (50/50 by weight) | 10 g |
| Total: | 100 g |

EXAMPLE 16

An after-shampoo is prepared in the form of an aerosol, with the following composition:

| | |
|---|---|
| Collagen hydrolysate containing trimethylammonium groups, called "Triethonium Hydrolyzed Collagen Ethosulfate" in the CTFA dictionary, sold under the name QUAT PRO E by the company MAYBROOK | 0.5 g AS |
| Cationic emulsion which is a combination: | |
| of Amodimethicone, of Tallowtrimonium, and of Nonoxinol 10, sold by the company DOW CORNING under the name DOW CORNING Q2 7224 at a concentration of 35% AS | 1.5 g AS |
| Distearyldimethylammonium chloride | 3 g AS |
| NaOH q.s. pH 7 | |
| Perfume, preserving agent, colorant q.s. | |
| Water q.s. | 100 g |

This composition is packaged as an aerosol:

| | |
|---|---|
| Above composition | 90 g |
| Propellant: Freons 12/114 (50/50 by weight) | 10 g |
| Total: | 100 g |

The foam in Examples 15 and 16 is applied to clean hair and left in contact for a few minutes. After rinsing, the sensitised wet hair is soft and lively and disentangles readily. It quickly acquires resilience while being dried.

The dry sensitised hair is soft, silky and shiny, disentangles easily and its ends are smooth.

The styling is resilient.

We claim:

1. A cosmetic composition for hair care comprising at least one water-dispersible cationic surfactant in proportions of from 0.05 to 7% by weight, at least one polypeptide carrying quaternary ammonium groups at the end of the chain or grafted on the chain in proportions of from 0.05 to 7% by weight, and at least one cationic silicone polymer in proportions from 0.05 to 7% by weight of the total weight of the composition, said one cationic silicone polymer being a product of the general formula:

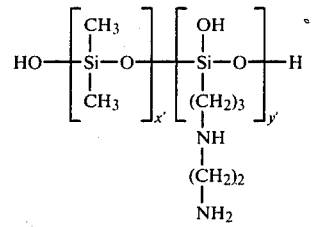

where x' and y' have average values such that the average molecular weight is from 5,000 and 10,000, (ii) a compound of formula:

$$R'_a G_{3-a} Si-OSiG_2)_n (OSiG_b R'_{2-b})_m O-SiG_{3-a} R'_a$$

in which:

G is H, OH, $C_{1-8}$ alkyl or phenyl, a is 0, 1, 2 or 3 b is 0 or 1 the sum (n+m) is from 1 to 2,000, where n is from 0 to 1,999, and m is from 2,000 to 1, R' is a monovalent group of formula $C_q H_{2q} L$ in which q is from 2 to 8, and, L is

N R''—$CH_2$—$CH_2$—N(R'')$_2$

N(R'')$_2$

N⊕(R'')$_3$A⊖

N⊕(R'')H$_2$A⊖ or

NR''CH$_2$—CH$_2$—N⊕R''H$_2$A⊖, in which R'' is H, phenyl, benzyl, or a saturated monovalent hydrocarbon group of from 1 to 20 carbon atoms, and, A⊖ is Cl⊖, Br⊖, I⊖ or F⊖, (iii) a product of general formula:

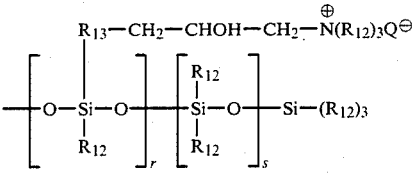

in which:

$R_{12}$ is a monovalent hydrocarbon group of from 1 to 18 carbon atoms, $R_{13}$ is a $C_1$-$C_{18}$ divalent hyrocarbon group, $Q^-$ is a halide ion, r is a mean statistical value of from 2 to 20, and s is a mean statistical value of from 20 to 200.

2. A composition according to claim 1, in which the water-dispersible cationic surfactant is of formula (I):

in which (1) $R_1$ is a product of general formula (II):

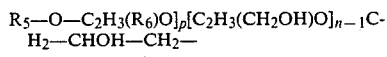

where $R_5$ is a straight- or branched-chain saturated or unsaturated aliphatic group of from 4 to 20 carbon atoms;

$R_6$ is
(i) an alkyl of from 4 to 20 carbon atoms,
(ii) a straight- or branched-chain alkoxymethyl group in which the alkoxy part is from 4 to 20 carbon atoms,
(iii)
a straight-chain alkenyloxy group in which the alkenyl part is from 4 to 20 carbon atoms;
p is from 1 to 2.5 and is a mean statistical value;
n is from 2 to 20 and is a mean statistical value;
$R_2$ is an alkyl or hydroxyalkyl group of from 1 to 3 carbon atoms;
$R_3$ and $R_4$, which may be identical or different, are each an alkyl or hydroxyalkyl group of from 1 to 3 carbon atoms or $R_3$ and $R_4$ form, with the nitrogen atom to which they are attached, a pyrrolidine, piperidine, morpholine or N-methylpiperazine heterocyclic ring;
$X^\ominus$ is an anion;

(2) $R_2$ and $R_3$ are each methyl, and
(i) $R_1$ and $R_4$ which may be identical or different are each a straight-chain saturated aliphatic group of from 12 to 22 carbon atoms or an aliphatic group derived from tallow fatty acids and containing from 14 to 22 carbon atoms, or
(ii) $R_1$ is a straight-chain saturated aliphatic group and $R_4$ is methyl or benzyl, (III)
$R_1$ is an alkylamidopropyl radical, the alkyl part containing from 14 to 22 carbon atoms and $R_4$ is an alkylacetate group, the alkyl part of which contains 12 to 16 carbon atoms, and $X^\ominus$ is a halide or $CH_3SO_4^\ominus$ anion;

(3)
$R_1$ is an alkylamidoethyl and/or alkenylamidoethyl group, where the alkyl and/or alkenyl group contains from 14 to 22 carbon atoms and is derived from tallow fatty acids, $R_2$ and $R_3$ together with the nitrogen atom to which they are attached form a substituted heterocyclic ring of the 4,5-dihydroimidazole type, $R_4$ is a $C_1$-$C_4$ alkyl, and,
$X^\ominus$ is $CH_3SO_4^\ominus$.

3. A composition according to claim 2, in which the water-dispersible cationic surfactant is selected from the group consisting of products of general formula (I), in which:
(a)
$R_1$ is $$R_5-O-C_2H_3(R_6)O]_p[C_2H_3(CH_2OH)]_{n-1}CH_2-CHOH-CH_2- \quad (II)$$

where
$R_5$ is $C_8H_{17}$ or $C_{10}H_{21}$,
$R_6$ is $C_{14}H_{29}$ or $C_{16}H_{33}$,
p is 1,
n is from 2 to 5,
$R_2$ is methyl,
$R_3$ and $R_4$ together with the nitrogen atom to which they are attached form a morpholino ring, and,
$X^\ominus$ is $CH_3SO_3^\ominus$ or $CH_3SO_4^\ominus$;
(b)
$R_1$ is $C_{10}H_{21}O-C_2H_3(C_{14}H_{29})O][C_2H_3(CH_2OH)O]CH_2CHOH-CH_2-$, $R_2$ is methyl,
$R_3$ and $R_4$ together with the nitrogen atom to which they are attached form a morpholino ring, and,
$X^\ominus$ is $CH_3SO_3^\ominus$;
(c)
$R_1$ is $C_{10}H_{21}-O-[C_2H_3(C_{14}H_{29})O][C_2H_3(CH_2OH)O]_4CH_2-CHOH-CH_2-$,
$R_2$ is methyl,
$R_3$ and $R_4$ together with the nitrogen atom to which they are attached form a morpholino ring; and,
$X^\ominus$ is $CH_3SO_3^\ominus$;
(d)
$R_1$ and $R_4$ which may be the same or different and each is a mixture of alkenyl and/or alkyl groups derived from tallow fatty acids and containing from 14 to 22 carbon atoms,
$R_2$ and $R_3$ are each methyl, and,
$X^\ominus$ is $Cl^\ominus$;
(e)
$R_1$ is an alkylamidoethyl and/or alkenylamidoethyl group where the alkyl and/or alkenyl part contains from 14 to 22 carbon atoms and is derived from tallow fatty acids;
$R_2$ and $R_3$ form, with the N atom to which they are attached, a 2-alkyl (derived from tallow fatty acids)-4,5-dihydroimidazole ring;
$R_4$ is a lower alkyl group of from 1 to 4 carbon atoms, and,
$X^\ominus$ is $CH_3SO_4^\ominus$, and
(f)
$R_1$ is a straight-chain saturated aliphatic group of 22 carbon atoms;
$R_2$, $R_3$ and $R_4$ are each methyl; and,
$X^\ominus$ denotes $Cl^\ominus$.

4. A composition according to claim 1, in which the quaternised protein is a polypeptide carrying one or more quaternary ammonium groups at the end of the chain or grafted on the chain, which are selected from the group consisting of:
a collagen hydrolysate carrying one or more triethylammonium or trimethylammonium and trimethylstearylammonium groups,
an animal protein hydrolysate carrying one or more trimethylbenzylammonium groups,
a protein hydrolysate carrying, on the polypeptide chain, one or more quaternary ammonium groups each containing at least one alkyl group of from 1 to 18 carbon atoms,
a quaternary protein of formula:

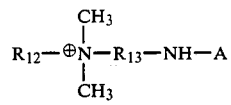

in which A is a protein residue derived from collagen protein hydrolysates, $R_{12}$ is a lipophilic group containing up to 30 carbon atoms, and $R_{13}$ is an alkylene group of from 1 to 6 carbon atoms.

5. A composition according to claim 1, in which the silicone polymer is
(i) a product of general formula:

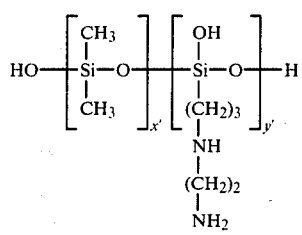

where x' and y' have average values such that the average molecular weight is from 5,000 and 10,000,
(ii) a compound of formula:

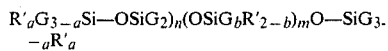

in which:
G is H, OH, $C_{1-8}$ alkyl or phenyl,
a is 0, 1, 2 or 3
b is 0 or 1
the sum (n+m) is from 1 to 2,000, where n is from 0 to 1,999, and m is from 2,000 to 1,
R' is a monovalent group of formula $C_qH_{2q}L$ in which q is from 2 to 8, and,
L is
N R"—$CH_2$—$CH_2$—N(R")$_2$
N(R")$_2$
$N^\ominus$(R")$_3A^\ominus$
$N^\ominus$(R")$H_2A^\ominus$, or,
NR"$CH_2$—$CH_2$—$N^\ominus$R"$H_2A^\ominus$,
in which R" is H, phenyl, benzyl, or a saturated monovalent hydrocarbon group of from 1 to 20 carbon atoms, and,
$A^\ominus$ is $Cl^\ominus$, $Br^\ominus$, $I^\ominus$ or $F^\ominus$,
(iii) a product of general formula:

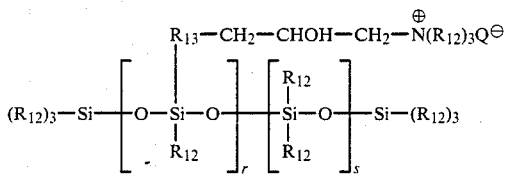

in which:
$R_{12}$ is a monovalent hydrocarbon group of from 1 to 18 carbon atoms,
$R_{13}$ is a $C_1$-$C_{18}$ divalent hydrocarbon group,
$Q^-$ is a halide ion,
r is a mean statistical value of from 2 to 20, and
s is a mean statistical value of from 20 to 200.

6. A composition according to claim 5 in which the silicone polymer is (ii) in which a is 0 and b is 1.

7. A composition according to claim 5, in which the silicone polymer is of the general formula:

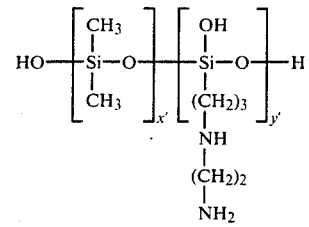

where x' and y' are as defined in claim 5, is combined with a trimethylalkylammonium chloride of general formula:

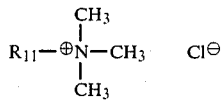

where $R_{11}$ is a mixture of alkenyl and/or alkyl groups of from 14 to 22 carbon atoms derived from tallow fatty acids,
and a polyethoxylated nonylphenol of formula:

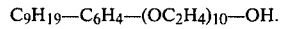

8. A composition according to claim 4, in which the silicon polymer is the trimethylsilylamodimethicone of general formula:

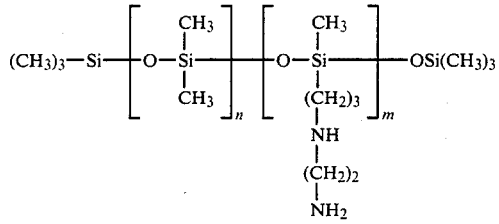

in which the sum (n+m) is from 1 to 2,000; where n is from 0 to 1,999 and m is from 2,000 to 1.

9. A composition according to claim 8, in which the trimethylsilylamodimethicone is combined with octoxynol 40, with isolaureth-6 and with ethylene glycol.

10. A composition according to claim 4, in which the silicone polymer is a polymer which has a flashpoint of 60° C., according to the ASTM Standard D-93, a viscosity of 11 centipoises at a concentration of 35% of active substance and at 25° C., and a total basicity value of 0.24 milliequivalent per gramme.

11. A composition according to claim 1, which contains one or more water-dispersible cationic surfactants in a proportion of from 0.05 to 7% by weight, one or more water-soluble quaternised proteins in a proportion of from 0.05 to 7% by weight and one or more cationic silicone polymers, in a proportion of from 0.05 to 7% by weight of the total weight of the composition.

12. A composition according to claim 1, which is in the form of a shampoo, a rinsing product to be applied before or after a shampoo, before or after dyeing or bleaching, or before or after premanent-waving or hair-straightening; a product for hair-setting setting or blow-drying, a restructuring composition, a product for permanent-waving or in a form that may be packaged as an aerosol.

13. A composition according to claim 1, which also contains one or more adjuvant which is an anionic, nonionic, amphoteric and/or zwitterionic surfactant, perfume, colorant, preserving agent, sequestering agent, thickener, emulsifier, softener, foam stabiliser, or propellant.

14. A composition according to claim 13, which is a shampoo containing anionic, nonionic, amphoteric and/or zwitterionic surfactant in an amount of from 3 to 50% by weight of the total weight of the composition.

15. A composition according to claim 14, in which the surfactant is present in an amount of from 3 to 20% by weight.

16. A composition according to claim 1, which is in the form of an aerosol and contains a propellant gas.

17. A hair treatment process, in which an effective amount of at least one composition according to claim 1 is applied to hair before the hair is shaped.

18. A hair treatment process, in which a suitable quantity of at least one composition according to claim 1 is applied to hair, and after a few minutes' application the hair is rinsed and dried.

19. A cosmetic composition for hair care comprising at least one water-dispersible cationic surfactant in proportions of from 0.1 to 3% by weight, at least one polypeptide carrying quaternary ammonium groups at the end of the chain or grafted on the chain in proportions of from 0.1 to 3% by weight and at least one cationic silicone polymer in proportions from 0.1 to 3% by weight of the total weight of the composition, said one cationic silicone polymer being a product of the general formula:

$$HO-\left[\begin{array}{c}CH_3\\|\\Si-O\\|\\CH_3\end{array}\right]_{x'}\left[\begin{array}{c}OH\\|\\Si-O\\|\\(CH_2)_3\\|\\NH\\|\\(CH_2)_2\\|\\NH_2\end{array}\right]_{y'}H$$

where x' and y' have average values such that the average molecular weight is from 5,000 and 10,000, (ii) a compound of formula:

$$R'_aG_{3-a}Si-OSiG_2)_n(OSiG_bR'_{2-b})_mO-SiG_{3-a}R'_a$$

in which:
G is H, OH, $C_{1-8}$ alkyl or phenyl,
a is 0, 1, 2 or 3
b is 0 or 1
the sum (n+m) is from 1 to 2,000, where n is from 0 to 1,999, and m is from 2,000 to 1,
R' is a monovalent group of formula $C_qH_{2q}L$ in which q is from 2 to 8, and
L is
 N R"—CH$_2$—CH$_2$—N(R")$_2$
 N(R")$_2$
 N$^\oplus$(R")$_3$A$^\ominus$
 N$^\oplus$(R")H$_2$A$^\ominus$or
 NR"CH$_2$—CH$_2$—N$^\oplus$R"H$_2$A$^\ominus$,
in which R" is H, phenyl, benzyl, or a saturated monovalent hydrocarbon group of from 1 to 20 carbon atoms, and,
A$^\ominus$ is Cl$^\ominus$, Br$^\ominus$, I$^\ominus$ or F$^\ominus$, (iii) a product of general formula:

$$(R_{12})_3-Si-\left[O-\begin{array}{c}R_{13}-CH_2-CHOH-CH_2-\overset{\oplus}{N}(R_{12})_3Q^\ominus\\|\\Si-O\\|\\R_{12}\end{array}\right]_r\left[\begin{array}{c}R_{12}\\|\\Si-O\\|\\R_{12}\end{array}\right]_s Si-(R_{12})_3$$

in which:
$R_{12}$ is a monovalent hydrocarbon group of from 1 to 18 carbon atoms,
$R_{13}$ is a $C_1$-$C_{18}$ divalent hydrocarbon group,
$Q^-$ is a halide ion,
r is a mean statistical value of from 2 to 20, and
s is a mean statistical value of from 20 to 200.

20. The cosmetic composition of claim 19, said composition comprising
from 0.1 to 3% by weight of dimethyl dialkyl ($C_{14}$-$C_{22}$) ammonium chloride, from 0.1 to 3% by weight of a quaternised protein having the formula:

$$R_{12}-\overset{CH_3}{\underset{CH_3}{\overset{|}{\underset{|}{\oplus N}}}}-R_{13}-NH-A,$$

in which
A denotes a protein residue derived from collagen protein hydrolysates, $R_{12}$ denotes a lipophilic group containing up to 30 carbon atoms, $R_{13}$ denotes an alkylene group containing 1 to 6 carbon atoms, of a molecular weight of from 1,500 to 10,000,
from 0.1 to 3% by weight of cationic emulsion which is a combination of a component of the formula:

$$HO-\left[\begin{array}{c}CH_3\\|\\Si-O\\|\\CH_3\end{array}\right]_{x'}\left[\begin{array}{c}OH\\|\\Si-O\\|\\(CH_2)_3\\|\\NH\\|\\(CH_2)_2\\|\\NH_2\end{array}\right]_{y'}H,$$

a component of the formula:

$$R_{11}-\overset{CH_3}{\underset{CH_3}{\overset{|}{\underset{|}{\oplus N}}}}-CH_3 \quad Cl^\ominus,$$

where
$R_{11}$ denotes a mixture of alkenyl and/or alkyl radicals containing from 14 to 22 carbon atoms, and,
a component of the formula $C_9H_{19}$—$C_6H_4$—$(OC_2H_4)_{10}$—OH.

* * * * *